United States Patent [19]
Daum et al.

[11] Patent Number: 5,961,455
[45] Date of Patent: Oct. 5, 1999

[54] DEVICE FOR POSITIONING A MEDICAL INSTRUMENT AND METHOD

[75] Inventors: Wolfgang Daum, Schwerin; Axel Winkel, Zapel Hof, both of Germany

[73] Assignee: Daum GmbH, Germany

[21] Appl. No.: 08/778,422

[22] Filed: Dec. 31, 1996

[51] Int. Cl.$^6$ .................................................. A61B 5/00
[52] U.S. Cl. ........................... 600/407; 600/414; 600/421
[58] Field of Search .............................. 128/653.1, 653.2, 128/653.5, 660.03, 898, 899, 664, 665; 378/163, 164, 165, 205, 206; 356/247, 248; 606/130; 600/407, 410, 421, 439, 473, 476, 414

[56] References Cited

U.S. PATENT DOCUMENTS

| | | |
|---|---|---|
| 4,506,676 | 3/1985 | Duska . |
| 4,618,978 | 10/1986 | Cosman . |
| 4,838,265 | 6/1989 | Cosman et al. . |
| 4,860,331 | 8/1989 | Williams et al. . |
| 5,034,969 | 7/1991 | Ozaki . |
| 5,105,457 | 4/1992 | Glassman . |
| 5,211,166 | 5/1993 | Sepponen . |
| 5,216,700 | 6/1993 | Cherian . |
| 5,239,569 | 8/1993 | Saleh et al. . |
| 5,299,253 | 3/1994 | Wessels . |
| 5,368,030 | 11/1994 | Zinreich et al. . |
| 5,394,457 | 2/1995 | Leibinger et al. . |
| 5,427,099 | 6/1995 | Adams . |
| 5,469,847 | 11/1995 | Zinreich et al. . |
| 5,556,372 | 9/1996 | Talish et al. . |

*Primary Examiner*—Marvin M. Lateef
*Assistant Examiner*—Shawna J Shaw
*Attorney, Agent, or Firm*—Merchant, Gould, Smith, Edell, Welter & Schmidt, P.A.

[57] ABSTRACT

The invention provides a device for correlating the internal location of an anatomical point of a human or animal patient with a location on the external body contours of the patient. In one embodiment, the invention is particularly suited for external positioning of a medical instrument for insertion into the patient's body to contact the anatomical point

15 Claims, 1 Drawing Sheet

DEVICE FOR POSITIONING A MEDICAL INSTRUMENT AND METHOD

FIELD OF THE INVENTION

The invention is directed to correlating the internal location of a normal or abnormal anatomical structure in a patient's body with an external marker. Specifically, the invention provides a device and method of using the device to position a medical instrument on the external body surface of a patient for insertion of the instrument into the patient's body to contact an internal structure.

BACKGROUND OF THE INVENTION

One problem faced by a radiologist, surgeon or other medical practitioner when inserting a medical instrument (device), such as a trocar, biopsy punch or biopsy needle, into a patient's body during MRI procedures is the difficulty of correlating the appropriate external position of the instrument to assure contact with the desired internal structure. The problem of correlation can also cause inadvertent contact of the instrument with an unintended internal structure.

Diagnostic imaging modalities such as magnetic resonance tomography (MRI) provide diagnostic images which show the location of an anatomical structure or location in a patient's body. Often times, however, it is difficult to transfer the point obtained from the image onto the body's contour. Accordingly, there is a need for a system to correlate an external body location with a particular internal site. There is also a need for a system to provide accurate positioning of a medical instrument on a patient's body to contact a desired internal point.

SUMMARY OF THE INVENTION

The present invention claims priority to DE 196 17 534.8, the disclosure of which is incorporated herein.

The invention provides a device for correlation of an external location of a patient's body with an internal point in the patient's body as identified on a diagnostic image. The disclosure further provides a method for using the device to externally position a medical instrument on a patient's body for insertion of the instrument into the patient's body to contact an internal point located on the diagnostic image.

In one embodiment, a device of the invention includes a plurality of hollow tubes, suitable for containing a positive contrast media, in a spaced-apart relationship defining an intermediate region.

Preferably, the hollow tubes are elongate structures spaced apart equally and parallel to one another. During use, the hollow tubes contain a positive contrast media and the intermediate regions are a neutral media. Typically, for MRI use, the positive contrast media includes a magnetically active component, for example, a lanthanide element such as gadolinium or lanthanum. The intermediate region can be transparent or void.

A device of the invention can be formed from at least two layers of plastic film, at least one of which is swedged, and the films longitudinally sealed to form the hollow tubes. A device of the invention can further include an adhesive layer for adhering the device to a patient's body. The adhesive layer can be permanently attached to the device or removable for reuse of the device. A device of the invention can also be prepared using known pour molding techniques.

The invention also provides a method for externally positioning a medical instrument on a patient's body for insertion of the instrument into the patient's body to contact an internal point located on a diagnostic image of the patient. According to the method, a device of the invention is applied to the patient's body in a region where a diagnostic image will be made. After the diagnostic image is taken, the location of an internal point relative to the external body contour is determined. Based on this determination, the medical practitioner can then appropriately position a medical instrument for insertion into the patient's body to contact the internal point. The device and method of the invention are particularly advantageous for use with a piercing medical instrument, such as a biopsy, punch, biopsy needle, or trocar.

DETAILED DESCRIPTION

Figure 1:
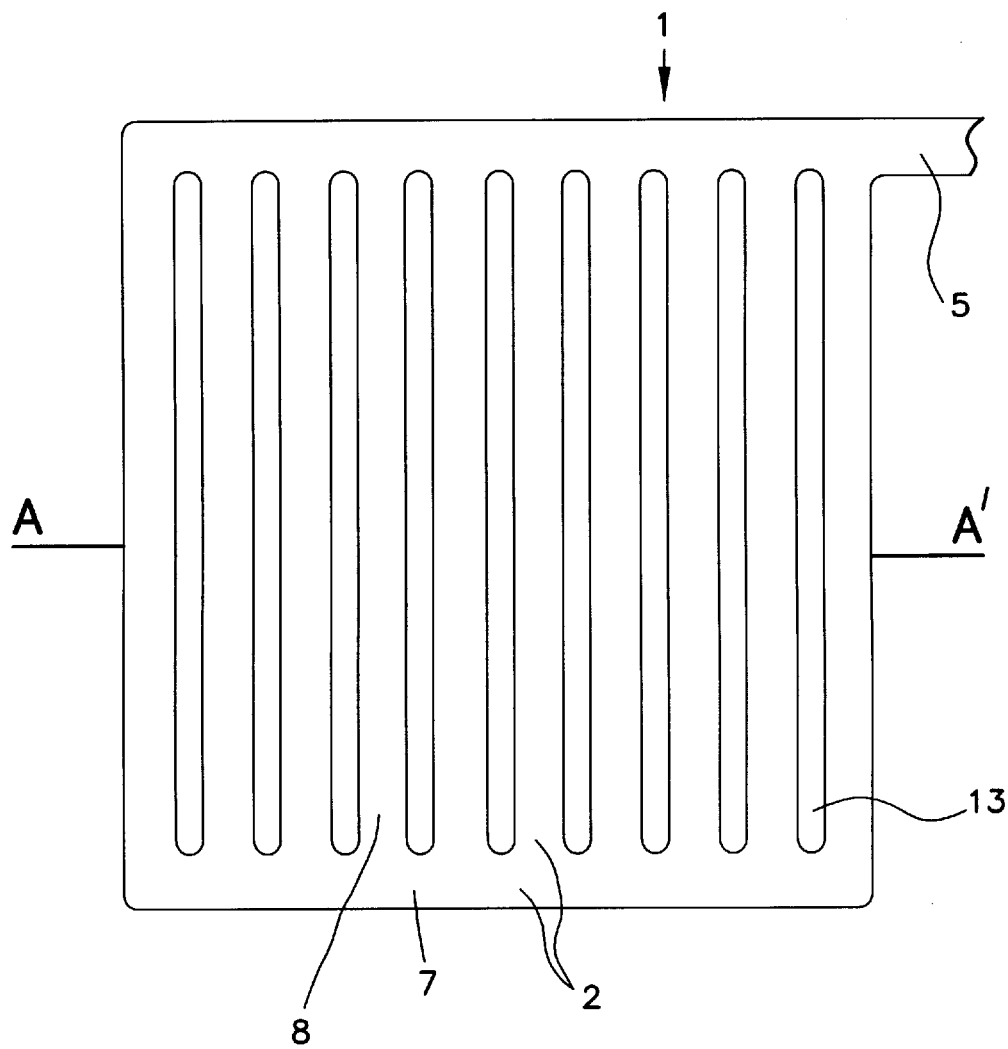
FIG. 1 is a top view of one embodiment of a device of the invention.

The present disclosure provides a device for correlating the location of an internal point in a patient's body with the patient's external body contours. The disclosure also provides a method for using the device to position a medical instrument that is used to penetrate the external body surface and contact the internal point. The device and method disclosed are suitable for human or animal use.

A device of the invention includes alternating regions of different contrast densities. In typical use, a device of the invention is applied to the skin of a patient overlying the body region where the diagnostic image will be taken. The device is generally positioned on the patient's skin in a plane perpendicular to the image plane of interest. The device creates alternating contrast densities on the diagnostic image which can be used as a measuring bar to accurately correlate the relative positions of a point on the external body contour of the patient and a particular internal point.

As used herein, the term "internal point" refers to any normal or abnormal anatomical structure or location which may be found internal to the skin and other integumentary layers of a human or animal body. "Normal anatomical structure" includes, for example, heart, blood vessels, lungs, thymus, liver, pancreas, spleen, kidneys, ovaries, adrenal glands, gut, lymph nodes, etc." Normal anatomical structure" also includes bones, ligaments, tendons, muscles and other structures related to the skeletal system. "Abnormal structure" includes tumors (benign or malignant), abscesses, hematomas, lipomas, etc. Normal and abnormal structures may be gas or fluid filled, or solid. The term "location" refers to non-structural points such as the retroperitoneal or pleural space. A "structure" or "location" can be defined or diffuse. Hence, as will be described below, a device disclosed herein can, for example, be used to locate a site on the external body contour of a patient which provides the most advantageous approach for biopsy of an osteoma in the tibia of the patient.

A device according to the invention is particularly advantageous when used with a medical instrument that is inserted internally into a patient's body without the use of a full exposure incision or endoscopic instrumentation. As used herein, a "medical instrument" includes any instrument used in the practice of medicine or surgery. Instruments typically used with a device of the invention include "piercing instruments," for example, a biopsy punch, biopsy needle, trocar, epidural needle, scalpel etc.

During use, a device of the invention includes components which produce regions of alternating contrast density on a diagnostic image. Typically, the device includes a positive contrast media in a spaced apart relationship with a neutral media. The neutral media is located between regions of positive contrast media. The region between positive contrast regions is also referred to as the "intermediate region".

As used herein, a "positive contrast media" refers to a media including a magnetically active component, such as paramagnetic metal ions, which produce density on a diagnostic image that is distinguishable from the density of the "neutral media". When applied to the external body surface of a patient during an imaging procedure, the distinction between the alternating densities of the device provides a measuring bar on the resulting diagnostic image for correlation of the external body contours with an internal point of interest. A magnetically active media includes liquid compositions based on lanthanide elements of the periodical table, for example, gadolinium, lanthanum, etc.

A "neutral media" includes any material which produces a density on the diagnostic image which is distinguishable from the positive contrast media, for example, magnetically nonactive components such as certain plastics or rubbers lacking paramagnetic ions. In one preferred embodiment, the alternating contrast regions of a device of the invention are substantially straight elongate structures which are parallel to one another. The device can also have a cross hatch arrangement of the positive contrast media.

A device of the invention can be of any size suitable to provide a herein disclosed measuring bar over the region of the body being imaged. The width dimension of the alternating regions of contrast media can vary. The smaller the width of each contrast region, the greater level of resolution provided in correlating an external body region with a particular internal point on the diagnostic image. In one embodiment, the spacing between alternating contrast regions is constant. A suitable width for the positive contrast regions is about 1 to 15 mm; a suitable width for the transparent region is about 1 to 15 mm.

The regions of positive (active) contrast media can be a liquid contrast media enclosed within a hollow tube (space) formed from a transparent or neutral media. Multiple hollow tubes can be interconnected with a transparent media in between.

A suitable material for preparing a hollow tube for containing a contrast media includes a film (foil) made of plastic, rubber or other similar material. In one embodiment, two opposing films are used. According to this embodiment, each film is "swedged" to form at least one longitudinally extending hemicircle shape which will form one half of a longitudinally extending hollow tube. There is an intermediate region between each hemicircle. The swedged films are then opposed in mirror image orientation and sealed together at the intermediate region between the swedges, along the longitudinal extent of the swedges to form the hollow tubes. The resulting hollow tubes are circular in cross section. The opposing films can be sealed using known sealing methods such as heat (weld) or glue.

In an alternative embodiment, only one of the two films is swedged. The second film remains flat. The swedged film is opposed to the flat film and the two films are sealed together along the longitudinal extent of the swedges at the intermediate region between the swedges. According to this embodiment, the resulting hollow tubes are hemispherical in cross section.

In another embodiment, opposing films can be prepared as above but in addition, a perimeter swedge which extends around the perimeter of the films is also formed. In a preferred embodiment, the resulting "perimeter" hollow tube is contiguous with one or both of the longitudinal ends of the hollow tubes. This arrangement advantageously provides for filling all tubes with a fluid contrast agent at any location on any tube.

A device according to the embodiments described which include hollow tubes for containing a positive contrast media can be prefilled with the contrast media and stored for use, or the tubes can be filled immediately prior to use.

The sealed film in the intermediate region of the device can remain if the material sufficiently neutral to provide the contrast function of the invention. Alternatively, the foil can be removed to create a "void" between the hollow tubes.

A device of the invention having hollow tubes for containing a positive contrast agent can also be prepared by known poured molding methods.

A device of the invention can further include an adhesive for adhering (sticking) the device to the skin of a patient. The adhesive can be applied directly to the device. Alternatively, the adhesive can be applied to a removable film which is replaceable for multiple use applications. Suitable adhesives for sticking the device to a patients body which are physiologically non-reactive are known.

DETAILED DESCRIPTION OF THE ILLUSTRATED EMBODIMENT

The invention will be further described by reference to the embodiments illustrated in FIGS. 1–3. This embodiment shows the device as a "grid" 1 of hollow spaces (tubes) 2. During use, these hollow spaces, contain a fluid which can produce a positive image contrast on an MRI image.

FIG. 1 is a top view of such a device. FIG. 2 is a cross-sectional view of the device shown in FIG. taken at axis AA'. FIG. 3 is a cross-sectional view of an alternate embodiment. In the embodiments shown, the device includes two opposing welded foils.

Figure 2:
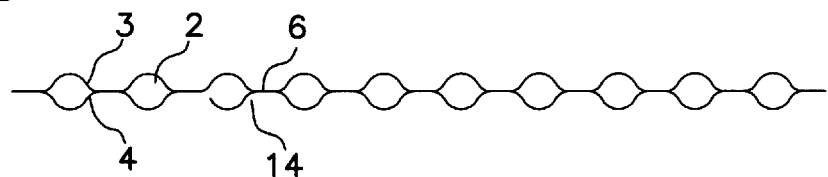
FIG. 2 is a cross-sectional view of the embodiment of the device of FIG. 1 taken at line AA'.

In FIG. 2, the upper foil 3 and the under foil 4 are swedged, opposed as inverted mirror images, and sealed by heat (weld) at the intermediate region 6 in such a manner that hollow spaces (tubes) 2 are formed. The hollow tubes contain an agent which contrasts with the intermediate region during use of the device. The hollow tubes can be filled with a contrast agent during the welding process or through an opening 5, which is closed and welded after the filling process. FIG. 1 shows the filler opening 5 as part of the perimeter tube 7 which is contiguous with the longitudinal tubes 8. In one embodiment, the grid includes hollow tubes which are about 7 mm wide, 145 mm long and spaced apart by an intermediate region about 10 mm wide.

Figure 3:
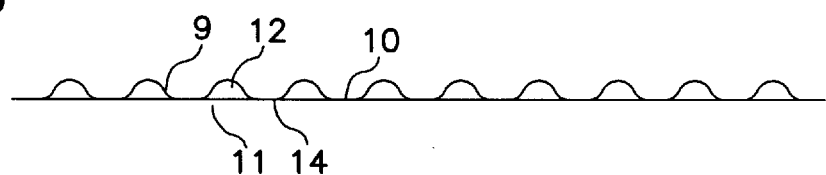
FIG. 3 is a cross-sectional view of another embodiment of a device of the invention.

FIG. 3 shows a second embodiment wherein only the upper foil 9 is swedged and welded at intermediate region 10 to flat lower foil 11 to form hemispherical shaped tubes, 12. Both the upper and lower foils can also be connected by gluing. Foil-free zones or "voids" 13 (FIG. 1) can be produced in the intermediate region by punching out the foil. In one embodiment, the foil is polyurethane.

The underside of the device (the side which is in contact with the patients skin during use), e.g., 14, can be coated with an adhesive layer or an adhesive coated film so that the device will adhere to the patient's skin for fixed positioning. When the device is adhered with under side 14 on the patient's skin, the hollow spaces 2 filled with a contrast agent are visible on the MRI image. To provide a preferred "measuring bar," the device is adhered to the patient's body with the plane of the device perpendicular to the MRI image plane of interest, and with the long axis of the hollow tubes perpendicular to the MRI image plane of interest.

A device of the invention is particularly useful for external positioning of a penetrating instrument to be inserted into a patient's body to contact a desired internal point. The most advantageous positioning of the instrument is typically determined by a medical practitioner based on the particular situation and particular result desired. As used herein, "contact" includes placement of the instrument at a particular internal site merely for location verification purposes. "Contact" also includes use of an instrument to perform a procedure such as a punch biopsy, aspiration biopsy, fluid drainage, or other purposes for which it is desired to insert a medical instrument into a patients body.

An example of use of a device of the invention for positioning a biopsy needle during open MRI is as follows. A device as shown in FIGS. 1–3 is adhered to the external body surface of a patient over the region of the body to be imaged. The plane of the device is oriented perpendicular to the MRI image plane of interest and the longitudinal axis of the hollow spaces is aligned perpendicular to the MRI plane of interest. The MRI image is taken. The appropriate external location for insertion of the biopsy needle is determined after assessing the relative location of the desired internal point with the hollow spaces (or intermediate regions) on the diagnostic image. The hollow spaces (or intermediate region) of the grid on the patient are then counted and the biopsy needle is positioned on the patient's body at an intermediate region and inserted for contact with the internal structure.

The device can be disposed of or reused as previously discussed, by using a removable adhesive layer.

The above specification provides a complete description of devices and methods of the invention. Since many embodiments can be made without departing from the spirit and scope of the invention, the invention resides in the claims hereinafter appended.

What is claimed is:

1. A method for externally positioning a medical instrument on a patient's body for insertion of said medical instrument to contact an internal point in the patient's body, said method comprising:
    (a) applying a device for correlation of an external location of the patient's body with the internal point in the patient's body that is identified on a diagnostic image of the patient's body, said device comprising:
        a hollow perimeter tube in a rectangular shape;
        a plurality of hollow tubes arranged within said rectangular shape of said hollow perimeter tube, said plurality of hollow tubes arranged parallel to one another and in a spaced apart relationship defining an intermediate region between said parallel hollow tubes; and
        a liquid positive contrast media within said hollow perimeter tube and said plurality of parallel hollow tubes, said positive contrast media selected from a lanthanide element;
    (b) imaging said internal point of the patient's body;
    (c) determining an appropriate intermediate region for external positioning of said medical instrument for contacting said internal point in the patient's body based on the location of said internal point relative to one or more of said hollow tubes filled with said positive contrast media and intermediate regions;
    (d) positioning said medical instrument on the patient's body at said appropriate intermediate region; and
    (e) inserting said medical instrument to contact said internal point.

2. The method according to claim 1, wherein said medical instrument is a piercing instrument.

3. The method according to claim 1 wherein said medical instrument is a biopsy punch, biopsy needle, trocar, epidural needle, trocar or scalpel.

4. The method according to claim 1 wherein the lanthanide element is gadolinium.

5. A device for correlation of an external location of a patient's body with an internal point in the patient's body that is identified on a diagnostic image of the patient's body, said device comprising:
    a hollow perimeter tube in a rectangular shape;
    a plurality of hollow tubes arranged within said rectangular shape of said hollow perimeter tube, said plurality of hollow tubes arranged parallel to one another and in a spaced apart relationship defining an intermediate region between said parallel hollow tubes; and
    a liquid positive contrast media within said hollow perimeter tube and said plurality of parallel hollow tubes, said positive contrast media selected from a lanthanide element.

6. The device according to claim 5 wherein said lanthanide element is gadolinium.

7. The device according to claim 5 wherein said hollow perimeter tube and said plurality of hollow parallel tubes each comprise at least two layers of a plastic film, at least one of said layers which is swedged, said at least two layers of plastic film longitudinally sealed to form said hollow tubes.

8. A device for correlation of an external location of a patient's body with an internal point in the patient's body that is identified on a diagnostic image of the patient's body, said device comprising:
    (a) a plurality of hollow tubes oriented in a single plane and in a spaced apart relationship, said spaced apart relationship defining an intermediate region, said hollow tubes containing a liquid positive contrast media selected from a lanthanide element
        wherein said hollow tubes comprise at least two opposing layers of plastic film, at least one of which is swedged, said two opposing films longitudinally sealed to form said hollow tubes.

9. A device for correlation of an external location of a patient's body with an internal point in the patient's body that is identified on a diagnostic image of the patient's body, said device comprising:
    (a) a plurality of hollow tubes oriented in a single plane and in a spaced apart relationship, said spaced apart relationship defining an intermediate region, said hollow tubes containing a liquid positive contrast media selected from a lanthanide element
wherein said device is molded.

10. The device according to claim 9 wherein said lanthanide element is gadolinium.

11. The device according to claim 9 further including an adhesive layer for adhering said device to said patient's body.

12. The device according to claim 11 wherein said adhesive layer is removable.

13. The device according to claim 8 wherein said lanthanide element is gadolinium.

14. The device according to claim 8 further including an adhesive layer for adhering said device to the patient's body.

15. The device according to claim 1 wherein said adhesive layer is removable.

* * * * *